(12) United States Patent
Buchtal et al.

(10) Patent No.: US 9,939,374 B2
(45) Date of Patent: Apr. 10, 2018

(54) DEVICE AND METHOD FOR FAST RECORDING OF AN ABSORPTION SPECTRUM OF A FLUID USING A PLURALITY OF ETALONS IN COMBINATION WITH A TUNABLE FABRY-PEROT INTERFEROMETER

(71) Applicant: Dräger Medical GmbH, Lübeck (DE)

(72) Inventors: Ralf Buchtal, Lübeck (DE); Peter Dreyer, Pansdorf (DE); Livio Fornasiero, Bliestorf (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 189 days.

(21) Appl. No.: 14/390,523

(22) PCT Filed: Apr. 4, 2013

(86) PCT No.: PCT/EP2013/057112
§ 371 (c)(1),
(2) Date: Oct. 3, 2014

(87) PCT Pub. No.: WO2013/150102
PCT Pub. Date: Oct. 10, 2013

(65) Prior Publication Data
US 2015/0300948 A1 Oct. 22, 2015

(30) Foreign Application Priority Data
Apr. 5, 2012 (DE) .................... 10 2012 007 030

(51) Int. Cl.
*G01N 21/3504* (2014.01)
*G01J 3/26* (2006.01)
(Continued)

(52) U.S. Cl.
CPC ............ *G01N 21/3504* (2013.01); *G01J 3/26* (2013.01); *G01J 3/42* (2013.01); *G01J 3/433* (2013.01);
(Continued)

(58) Field of Classification Search
CPC ....... G01N 21/3504; G01N 2021/3518; G01N 21/3518; G01N 2021/355;
(Continued)

(56) References Cited

U.S. PATENT DOCUMENTS 3,914,055 A 10/1975 Wolga et al.
4,035,643 A * 7/1977 Barrett ...................... G01J 3/26
250/339.13
(Continued)

FOREIGN PATENT DOCUMENTS

CN 101806725 A 8/2010
CN 102230889 A 11/2011
(Continued)

*Primary Examiner* — Michael P Lapage
(74) *Attorney, Agent, or Firm* — McGlew and Tuttle, P.C.

(57) ABSTRACT

A device for recording an absorption spectrum of a fluid has a radiation source (1) that emits a radiation in a spectral range along a beam path (11), a measuring path (5), along which the radiation passes through the fluid and arranged in the beam path, a tunable Fabry-Perot interferometer (7), arranged in the beam path and transmitting radiation in the spectral range as a displaceable bandpass filter, and a detector (9, 35) measuring the intensity of the radiation in the spectral range. An etalon (3) is arranged for spectral modulation of radiation in the beam path and has a plurality of transmission maxima (17) in the spectral range. The bandpass filter, formed by the Fabry-Perot interferometer (7), is displaceable across the spectral range such that spectral
(Continued)

modulation of the radiation by the etalon (3) is measured by the detector (9, 35) as a modulation of radiation intensity over time.

20 Claims, 4 Drawing Sheets

(51) Int. Cl.
  *G01J 3/42* (2006.01)
  *G01J 3/433* (2006.01)
(52) U.S. Cl.
  CPC . *G01N 2201/061* (2013.01); *G01N 2201/068* (2013.01); *G01N 2201/0662* (2013.01)
(58) Field of Classification Search
  CPC .. G01N 2021/451; G01N 21/45; G01N 21/61; G01N 2201/0662; G01N 2201/068; G01N 2201/061; G01J 3/26; G01J 2003/262; G01J 3/433; G01J 3/42
  See application file for complete search history.

(56) References Cited

U.S. PATENT DOCUMENTS

| | | | |
|---|---|---|---|
| 4,525,067 A | 6/1985 | Hernandez | |
| 4,999,013 A * | 3/1991 | Zoechbauer | G01J 3/26 356/454 |
| 5,128,798 A * | 7/1992 | Bowen | G02B 5/288 356/519 |
| 5,218,422 A | 6/1993 | Zoechbauer | |
| 5,602,647 A * | 2/1997 | Xu | G01N 21/0303 356/246 |
| 5,606,419 A | 2/1997 | Foosnæs et al. | |
| 5,646,729 A * | 7/1997 | Koskinen | G01J 3/26 356/454 |
| 5,886,247 A * | 3/1999 | Rabbett | G01N 21/3504 250/339.13 |
| 6,147,351 A * | 11/2000 | Huiku | G01N 21/0303 250/343 |
| 6,447,698 B1 * | 9/2002 | Ihara | C09K 11/574 252/301.36 |
| 2004/0042083 A1 * | 3/2004 | Turner | G02B 5/284 359/578 |
| 2004/0145741 A1 | 7/2004 | Cole et al. | |
| 2004/0228375 A1 * | 11/2004 | Ghosh | H01S 3/136 372/32 |
| 2008/0074647 A1 | 3/2008 | Doring et al. | |

FOREIGN PATENT DOCUMENTS

| | | |
|---|---|---|
| DE | 39 25 692 C1 | 8/1990 |
| DE | 10 2006 045253 B3 | 12/2007 |
| DE | 10 2009 011421 B3 | 4/2010 |
| JP | H9-79980 A | 3/1997 |
| JP | 2003501622 A | 1/2003 |
| JP | 2004309296 A | 11/2004 |
| JP | 2005321244 A | 11/2005 |
| JP | 2008026397 A | 2/2008 |
| JP | 2010-169625 A | 8/2010 |
| JP | 2010-286291 A | 12/2010 |

\* cited by examiner

DEVICE AND METHOD FOR FAST RECORDING OF AN ABSORPTION SPECTRUM OF A FLUID USING A PLURALITY OF ETALONS IN COMBINATION WITH A TUNABLE FABRY-PEROT INTERFEROMETER

CROSS REFERENCE TO RELATED APPLICATIONS

This application is a United States National Phase application of International Application PCT/EP2013/057112 filed Apr. 4, 2013 and claims the benefit of priority under 35 U.S.C. § 119 of German Patent Application DE 10 2012 007 030.6 filed Apr. 5, 2012, the entire contents of which are incorporated herein by reference.

FIELD OF THE INVENTION

The present invention pertains to a device for recording an absorption spectrum of a fluid with a first radiation source, which emits a radiation in a first spectral range along a first beam path, with a first measuring section, which is arranged in the first beam path and along which the radiation passes through the fluid, with a tunable Fabry-Perot interferometer, which is arranged in the first beam path and which can transmit radiation in the first spectral range as a displaceable bandpass filter, and with a first detector for measuring the intensity of the radiation in the first spectral range, as well as to a method for recording an absorption spectrum of a fluid.

BACKGROUND OF THE INVENTION

It is often necessary in medical engineering to determine or monitor the concentration of selected components of the breathing air. For example, the concentration of the anesthetic gases being used in the breathing air is often measured during each breath in case of anesthetized patients or the alcohol content in the breathing air is measured when testing automobile drivers. Spectrometric methods are used to determine the concentration of the respective components. As a rule, signals are recorded for this with discrete filters in wavelength bands in which the gases have absorptions, and compared with references. The concentration of the gas in the breathing air can thus be inferred from the change in the signals at these wavelengths, which are characteristic of a certain gas.

A number of devices, with which the concentrations of selected components of a fluid or of a gas, for example, breathing gas, can be determined by absorption measurements at selected wavelengths or even over a spectral range, are known from the state of the art. Such devices have a radiation source, which emits radiation over a selected, continuous spectral range. An optical bandpass filter, called filter below for short, which limits the spectrum of the radiation to a wavelength that is characteristic of a component of the gas, whose concentration shall be measured, is arranged between the radiation source and a measuring section arranged downstream, in which the radiation passes through the fluid. After the radiation has passed through the filter and the measuring section, its intensity is measured with a suitable detector. The concentration of the component in the fluid can now be inferred from the attenuation of the intensity compared to a reference measurement in a reference fluid, in which the concentration of the component is known.

If the concentration of a plurality of components is to be measured, a separate, suitable filter must be used for each component. To determine the concentration of the various components within a short time period, possibly during one breath as a so-called measurement resolved for individual breaths, the different filters are arranged on a so-called filter wheel. A filter wheel is a rotating disk, which moves the filters in a rapid sequence into the beam path between the radiation source and the detector. This has, however, the drawback that only a small number of components can be analyzed, because a separate filter must be present for each component, and the size of the filter wheels is limited. In addition, the use of mechanical components is generally disadvantageous, because these increase the amount of maintenance needed and are prone to error.

A full absorption spectrum can be recorded with the use of a tunable Fabry-Perot interferometer, as it is described in DE 10 2006 045 253 B3. A tunable Fabry-Perot interferometer is arranged for this instead of a filter in the beam path between the radiation source and the detector. A Fabry-Perot interferometer is a device that has two partially transparent mirrors arranged in parallel to one another, whose reflective coated mirror surfaces point towards each other. The distance between the mirror surfaces determines a narrow wavelength range, which is transmitted by the Fabry-Perot interferometer and for which the Fabry-Perot interferometer is permeable. The width of the wavelength range passed through by the Fabry-Perot interferometer is called spectral resolution and depends on the wavelength. The distance between the mirror surfaces can be varied in a tunable Fabry-Perot interferometer and the wavelength range that is transmitted can thus be displaced. Thus, a Fabry-Perot interferometer is a displaceable bandpass filter, whose width corresponds to the spectral resolution of the Fabry-Perot interferometer. If the absorption spectrum of a fluid is to be detected completely over a selected spectral range, the Fabry-Perot interferometer only needs to be tuned over the selected spectral range.

In case of suitable coating of the mirror surfaces, a Fabry-Perot interferometer may also be permeable for two different wavelength ranges at the same time. It is consequently possible to record the absorption spectra of the fluid in both wavelength ranges simultaneously. A device for recording an absorption spectrum of a fluid with the use of such a Fabry-Perot interferometer is known from DE 10 2009 011 421 B3.

To determine the concentration of the individual components of the fluid, the spectrum recorded by the detector must be compared with a reference measurement. Lock-in amplifiers are routinely used for this. A measured signal is multiplied in a lock-in amplifier by a reference signal, and the result of the multiplication is integrated in a low pass filter. The lock-in amplifier consequently forms the cross correlation between the measured signal and the reference signal.

To make it possible to use a lock-in amplifier, the signal sent by the detector and hence the radiation emitted by the radiation source must, however, be modulated over time. Modulation over time shall be defined here as a change in the intensity of the radiation over time. This can be carried out in the simplest case by switching the radiation source on and off or by a chopper arranged downstream, which repeatedly interrupts the beam path between the radiation source and the detector.

The absorption of selected components in the breathing air is preferably measured at wavelengths between 2 μm and 15 μm. The broad-band radiation sources available in this wavelength range are usually thermal radiators. If these are modulated electrically over time with a frequency of more than 100 Hz that is necessary for measurements resolved for individual breaths, the relative modulation of the intensity depends strongly on the wavelength being considered, and the modulation decreases from short wavelengths to long ones. The intensity modulation decreases so strongly at longer wavelengths in the spectral range between 2 µm and 15 µm at frequencies of 100 Hz and higher that it is no longer sufficient for use with a lock-in amplifier.

Even though the use of a mechanical chopper is possible, in principle, this is again a mechanical component, which requires great maintenance efforts and is, moreover, difficult to miniaturize.

A similar problem arises when a photoacoustic or pyroelectric sensor is used as the detector, because these two types of sensors can only be used if the radiation has a change in intensity over time.

SUMMARY OF THE INVENTION

Thus, an object is to modulate the radiation emitted by the radiation source over the entire selected spectral range so fast over time that a photoacoustic sensor or a pyroelectric sensor arranged in the measuring section can be used as the detector. Furthermore, one object of the present invention is to modulate the radiation over time so fast that a lock-in amplifier arranged downstream can be used to compare the measured absorption spectrum with a reference spectrum.

The object is accomplished by a device that has a first etalon for the spectral modulation of the radiation, which is arranged in the first beam path and which has a plurality of transmission maxima in the first spectral range. Furthermore, the Fabry-Perot is set up for the bandpass filter formed by the Fabry-Perot interferometer to be able to be displaced over the first spectral range such that the spectral modulation of the radiation by the first etalon can be measured as a modulation over time of the intensity of the radiation by the first detector.

The device has, first, a first radiation source, which emits a radiation with a preferably continuous spectrum in a first spectral range. For example, membrane radiators, which have a continuous spectrum in a wavelength range between 2 µm and 20 µm, are suitable as the first radiation source for determining the concentration of components of the breathing air. High-performance helical radiators or other thermal radiators, which likewise have emission in this spectral range, may also be used as an alternative. The radiation emitted by the radiation source is preferably collimated by a lens array or a reflector and led through the device along a first beam path.

The first measuring section arranged in the first beam path may be, for example, a cuvette, in which the fluid to be analyzed is accommodated.

An etalon shall be defined here as a Fabry-Perot interferometer, in which the distance between the mirror surfaces cannot be changed or is not changed during a measurement. For example, an uncoated, polished thin wafer, which consists of silicon or germanium or contains mainly silicon or germanium, may be used as the etalon. For example, metal-coated or dielectrically coated wafers, which are optically transparent, or two coated or uncoated, parallel plates located at spaced locations from one another, may also be used as etalons as an alternative. It is also conceivable to use, instead of an etalon, optical components, which have a comb-like transmission or reflection, for example, certain plastic films or even cuvettes filled with a gas, where the gas has a pronounced comb-like absorption.

The first etalon has a transmission maxima in the first spectral range. A broad-band radiation, which passes through the first etalon, thus undergoes subsequently a spectral modulation, which is characterized by a change of intensity minima and maxima specific of the etalon. Spectral modulation shall be defined here as the dependence of the intensity of a radiation on the wavelength or frequency. For example, a silicon wafer with a thickness of 100 µm has 35 transmission maxima and just as many transmission minima in the spectral range between 4 µm and 5 µm. The same wafer has 25 transmission maxima in the spectral range between 8 µm and 11 µm.

It is conceivable that the first etalon is designed such that at least some of the transmission maxima of the first etalon comprise wavelengths that are characteristic of the components whose concentration in the fluid shall be analyzed. The concentration of components of the fluids that have only narrow characteristic absorption lines can also be determined in an optimized manner in this way.

The first etalon is preferably such that the distance of the transmission maxima is greater than the spectral resolution of the Fabry-Perot interferometer in the first spectral range. If the spectral resolution of the Fabry-Perot interferometer is broader than the distance of the transmission maxima, this leads to an undesired smoothing of the spectrum. In other words, the intensity maxima generated by the first etalon appear broader and flatter when scanning with the Fabry-Perot interferometer.

The surfaces of the first etalon are preferably not aligned in parallel to the surfaces of the elements arranged in the direction of radiation propagation directly in front of and behind the first etalon in order to avoid additional undesired etalon effects.

Furthermore, a Fabry-Perot interferometer, in which the distance between the mirror surfaces can be set such that the Fabry-Perot interferometer represents a displaceable band-pass filter in the first spectral range, is arranged in the first beam path. The bandpass filter formed by the Fabry-Perot interferometer can now be displaced over the first spectral range, preferably continuously, such that the spectral modulation by the first etalon is measured by the first detector as a modulation over time of the intensity of the radiation. In other words, the spectral modulation of the radiation by the first etalon is rendered by the tuning of the Fabry-Perot interferometer and displacement of the bandpass filter that is associated with it into an intensity modulation of the radiation over time. The transmitted wavelength and hence the wavelength of the radiation can in this case be inferred based on the known width of the Fabry-Perot interferometer at any point in time.

If, for example, the Fabry-Perot interferometer is tuned five times per second over the spectral range from the shortest to the longest wavelength and back again in a device with a first etalon made of a silicon wafer with a thickness of 100 µm, which has 35 transmission maxima and minima in a spectral range between 4 µm and 5 µm, this corresponds to an intensity modulation of the radiation with a frequency of 350 Hz. The same silicon wafer has, for example, 25 transmission maxima and minima in a spectral range that comprises the wavelengths between 8 µm and 11 µm. Tuning the Fabry-Perot interferometer five times over this spectral range in both directions would thus correspond to an intensity modulation of the radiation with a frequency of 250 Hz.

Furthermore, the device has a first detector, which is arranged such that it can measure the intensity of the radiation after this has passed through the first etalon, the Fabry-Perot interferometer, and the first measuring section. The first detector may be, for example, a semiconductor sensor, a thermopile, a thermal resistor, a pyroelectric sensor or a photoacoustic gas sensor. The latter is preferably arranged in the first measuring section.

Such a device is advantageous because it has no micromechanical elements and it is nevertheless possible to modulate the intensity of the radiation with a frequency that is sufficiently high for a measurement resolved for individual breaths over a broad spectral range. Since macromechanical components are omitted, the device operates almost without wear, as a result of which the amount of maintenance needed is markedly reduced compared to devices known from the state of the art and the service life is prolonged.

In a preferred embodiment, a first lock-in amplifier is provided for determining the absorption spectrum of the fluid from the radiation intensities measured with the first detector. The lock-in amplifier forms the cross correlation function between the measured signal sent by the first sensor and a reference signal and represents an especially narrow bandpass filter, which permits even slight deviations between the measured signal and the reference signal to be detected even in case of signals with a large noise component. The lock-in amplifier makes it therefore possible in an especially advantageous manner to record an absorption spectrum of the fluid.

In another preferred embodiment, the device has a second radiation source, which emits a radiation in a second spectral range along a second beam path; a second measuring section, along which the radiation emitted by the second radiation source passes through the fluid; and a second detector for measuring the intensity of the radiation in the second spectral range. The first and second beam paths are designed in this case such that the Fabry-Perot interferometer is arranged in the first and second beam paths. As a displaceable bandpass filter, the Fabry-Perot interferometer can transmit radiation in the second spectral range. Furthermore, the device has a second etalon for the spectral modulation of the radiation, which is arranged in the second beam path and which has a plurality of transmission maxima in the second spectral range. In addition, the Fabry-Perot is set up such that the bandpass filter formed by the Fabry-Perot interferometer can be displaced over the second spectral range such that the spectral modulation of the radiation by the second etalon can be measured by the second detector as a modulation over time of the intensity of the radiation.

This preferred embodiment has a second radiation source, which emits radiation in a second spectral range, wherein the second spectral range preferably comprises wavelengths different from those of the first spectral range. For example, the first spectral range could comprise the wavelengths between 2 µm and 6 µm, preferably between 4 µm and 5 µm, and the second spectral range the wavelengths between 7 µm and 15 µm, preferably between 8 µm and 11 µm. It is also conceivable that the first radiation source and the second radiation source emit radiation over the same spectral range and are limited to the respective spectral ranges by corresponding bandpass filters only.

Furthermore, the device has a second etalon, which is arranged in the second beam path and which modules radiation in the second spectral range in a manner similar to the modulation of the radiation by the first etalon in the first spectral range. In particular, the second etalon has a plurality of transmission maxima in the second spectral range, the distance between which is greater than the bandwidth or even the spectral resolution of the Fabry-Perot interferometer in the second spectral range. It is, furthermore, conceivable that the second etalon is designed such that at least some of the transmission maxima of the second etalon comprise wavelengths that are characteristic of the components whose concentration in the fluid shall be analyzed.

The surfaces of the second etalon are preferably also not aligned in parallel to the surfaces of the elements arranged directly in front of and behind the second etalon in the direction of radiation propagation in order to avoid additional undesired etalon effects.

This preferred embodiment has, furthermore, a second measuring section, along which the radiation emitted by the second radiation source passes through the fluid. It is conceivable in this connection that the first and second measuring sections have equal length, the length of a measuring section being defined here as the section that the radiation travels along the measuring section through the fluid. The first measuring section is made integrally with the second measuring section in a preferred embodiment, i.e., the first and second measuring sections coincide or extend over the same path through the fluid. Such a device is especially advantageous because the absorption spectra in the fluid can be measured in two spectral ranges in the same measuring section and it is thus ensured that the concentration measurement is not affected by local differences in the concentration of the components.

However, it is also conceivable that the first and second measuring sections have different lengths. The latter is especially advantageous if the fluid has different absorptions in the first spectral range and in the second spectral range. It is thus conceivable, for example, that a component of the fluid, whose concentration shall be determined, has only a very weak absorption in the first spectral range. To nevertheless obtain measurable changes in absorption for the first detector, a longer first measuring section is used. Conversely, it is also conceivable that, for example, the concentration of a component of the fluid that has strong absorption at a low concentration in the second spectral range shall be determined. The second measuring section could be selected as a correspondingly short measuring section in this case, so that changes in absorption that are still measurable by the second detector will occur even at high concentrations.

The Fabry-Perot interferometer is arranged in the first and second beam paths in this preferred embodiment of the present invention. In other words, both the radiation emitted by the first radiation source and the radiation emitted by the second radiation source pass through the Fabry-Perot interferometer, and the first and second beam paths extend in parallel, nearly parallel or one above the other through the Fabry-Perot interferometer.

It is thus conceivable, for example, that the first and second beam paths reach the same beam splitter after the radiation has passed through the respective etalon. The beam splitter is arranged here, for example, such that the component of the radiation emitted by the first radiation source, which component is transmitted by the beam splitter, forms the first beam path in the Fabry-Perot interferometer, while the component of the radiation emitted by the second radiation source, which component is reflected by the beam splitter, forms the second beam path there.

The device has, moreover, a second detector, which is suitable for measuring the intensity of the radiation in the second spectral range after this radiation has passed through the second measuring section and the Fabry-Perot interferometer.

Furthermore, the Fabry-Perot interferometer is designed such that the distance between the mirror surfaces can be set such that the Fabry-Perot interferometer represents a displaceable bandpass filter in the second spectral range. The bandpass filter formed by the Fabry-Perot interferometer can be displaced here over the second spectral range, preferably continuously, such that the spectral modulation by the second etalon is measured by the second detector as a modulation over time of the intensity of the radiation. In other words, the spectral modulation of the radiation by the second etalon is rendered into a modulation of the radiation time with the tuning of the Fabry-Perot interferometer and the displacement of the bandpass filter that is associated with it.

In a preferred embodiment, the Fabry-Perot interferometer is designed such that it can transmit radiation in the first and second spectral ranges simultaneously and that the bandpass filter formed by the Fabry-Perot interferometer can be displaced simultaneously over the first and second spectral ranges such that the spectral modulation of the radiation by the first and second etalons can be measured by the first and second detectors as a modulation over time of the intensity of the radiation. In other words, the distance between the mirror surfaces of the Fabry-Perot interferometer can be set such that it forms a bandpass in the first and second spectral ranges simultaneously. The first and spectral ranges can thus be scanned simultaneously and the absorption spectrum of the fluid can be recorded in both spectral ranges in an especially short time, as a result of which it is possible to measure the concentration of components in a fluid whose composition changes at very short time intervals.

A second lock-in amplifier is used in another preferred embodiment to determine the absorption spectrum of the fluid from the radiation intensities measured with the second detector.

It is advantageous, furthermore, to design the first etalon integrally with the second etalon. In other words, only one etalon, which has a plurality of transmission maxima in both the first and second spectral ranges, is provided instead of the first and second etalons. For example, it would be possible to use a silicon wafer with a thickness of 100 μm, which has 35 transmission maxima in the spectral range between 4 μm and 5 μm and 25 transmission maxima in the spectral range between 8 μm and 11 μm. The overall size of the device can be markedly reduced hereby.

It is especially preferred if the first etalon is arranged in the first and second beam paths as a beam splitter such that the first and second beam paths extend in parallel behind the first etalon in the direction of radiation propagation. In other words, the first and second etalons are replaced by a common etalon, which is also designed as a beam splitter at the same time and merges the first and second beam paths such that the Fabry-Perot interferometer, which is located behind the etalon in the direction of radiation propagation, is passed through by the radiation emitted by the first and second radiation sources in parallel. Such a device is also especially advantageous, because an especially compact design can be obtained in this manner.

It is likewise preferred to design the first detector integrally with the second detector. In other words, only one detector, which measures the intensity of the radiation in both the first and second spectral ranges, is provided instead of a first detector and a second detector, as a result of which an especially compact design of the device is possible.

It is preferred, furthermore, for the first radiation source to be identical to the second radiation source. In other words, only one radiation source, which emits radiation in the in the first and second ranges, is provided instead of two radiation sources. An especially compact design can be obtained hereby as well.

In a preferred embodiment, the first radiation source is a thermal radiator, whose intensity can be modulated over time so fast that the relative change in the intensity of the radiation is more pronounced in one of the two spectral ranges than in the other spectral range. If only one radiation source is present and this is designed as a thermal radiator, it is advantageous to modulate the intensity of the radiation fast over time. If the modulation frequency is high enough, the intensity modulation affects only the shorter-wave spectral range, while the longer-wave spectral range of the two spectral ranges is not essentially modulated. If a detector records a superposition of the absorption spectra in the first and second spectral ranges, this additional modulation of the shorter-wave spectral range can be used in an especially advantageous manner to separate the first and second absorption spectra from one another.

The device may also be designed such that the absorption of the fluid can be determined in additional spectral ranges. The device has for this a radiation source, which emits radiation in the spectral range along a beam path, for each further spectral range. A measuring section, an etalon and a detector are arranged along each beam path, and the radiation passes through the fluid along the measuring section, the etalon has a plurality of transmission maxima for modulating the radiation in the spectral range, and the detector is set up to measure the intensity of the radiation in the spectral range. The beam paths are designed in this case such that the Fabry-Perot interferometer is arranged in each beam path. The Fabry-Perot interferometer is set up to transmit radiation in each of the spectral ranges as a displaceable bandpass filter, and the bandpass filter can be displaced over the spectral ranges such that the spectral modulation of the radiation by the etalon can be measured by the detectors as a modulation over time of the intensity of the radiation. It is conceivable in such a device that all radiation sources, all etalons, all measuring sections and/or all detectors are made integrally with one another, as a result of which a broadband device can be obtained in an especially compact design for recording absorption spectra.

The object is accomplished, furthermore, by a method for using a device according to the present invention, in which the Fabry-Perot interferometer is tuned such that the bandpass filter formed by the Fabry-Perot interferometer is displaced over the first spectral range such that the spectral modulation of the radiation by the first etalon is measured by the first detector as a modulation over time of the intensity of the radiation.

A measured signal sent by the second detector is compared with a reference signal with the first lock-up amplifier in a preferred embodiment for determining the absorption spectrum in the first spectral range.

The reference signal needed for this can be determined in various manners. The intensity maxima of the radiation, which are generated by the first etalon and the Fabry-Perot interferometer, do not, as a rule, occur at a constant time interval. It is therefore impossible, as a rule, to use an external reference signal with a constant frequency. It is, however, conceivable to adjust the control of the Fabry-Perot interferometer such that the maxima of the intensity-modulated radiation will occur at equal time intervals. It would be possible in this case to use a reference signal with constant frequency.

It is also possible as an alternative to record first an entire absorption spectrum for the first spectral range and to transform it with an analyzing unit such that the intensity maxima will be spaced equally over time. The measured signal generated in this manner can likewise be compared with an externally generated reference signal.

It is also conceivable to record first an absorption spectrum in which the first or second measuring section is filled with a reference fluid of known composition or is evacuated, and the measured signal sent by the detector in the process is used as a reference signal for further measurements.

If no lock-in amplifier is used, it is also conceivable to determine an absorption spectrum, in which integration is performed over the intensity maxima measured by the detector. If the width of the Fabry-Perot interferometer at the point in time at which an intensity maximum appears is known, the wavelength that is transmitted with this setting of the Fabry-Perot interferometer and thus also the wavelength at which the respective intensity maximum occurs can be inferred from that point in time. If integration is now performed over the entire intensity maximum, i.e., from one intensity minimum to the next, the relative absorption at the wavelength can be inferred from the comparison of the value of the integral with a reference measurement and a full absorption spectrum can be generated in the first spectral range, without a lock-in amplifier being necessary.

In another preferred embodiment, the Fabry-Perot interferometer is tuned such that the bandpass filter formed by the Fabry-Perot interferometer is displaced over the second spectral range such that the spectral modulation of the radiation by the second etalon is measured by the second detector as a modulation over time of the intensity of the radiation. It is, furthermore, also preferred in this embodiment if a measured signal sent by the detector is compared with a reference signal with the second lock-in amplifier.

Moreover, it is especially preferred that the Fabry-Perot interferometer is tuned such that the absorption spectrum of the fluid can be determined in the first and second frequency ranges simultaneously. This embodiment is especially advantageous because it permits an absorption spectrum of the fluid to be recorded in the first and second spectral ranges in an especially short time.

This is also possible especially if only one detector is used to measure the intensity of the radiation in the first and second spectral ranges, because the intensity modulation of the radiation is carried out by a first etalon and a second etalon, which may also be made integrally (i.e., as one element). An individual detector first measures a superposition of the absorption spectra in the first and second spectral ranges. However, since the intensity maxima of the radiation have different distances, depending on the spectral range, after passage through the etalon or etalons, the absorption spectra can be separated after recording in a simple manner. This may be carried out electronically, via a Fourier analysis or via two lock-in amplifiers, which use reference signals characteristic of the respective spectral range. Consequently, the frequency modulation may also be used for a Fourier analysis of the signal sequence in this connection for the lock-in method, besides the amplitude modulation.

The present invention will be explained below on the basis of drawings showing four exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
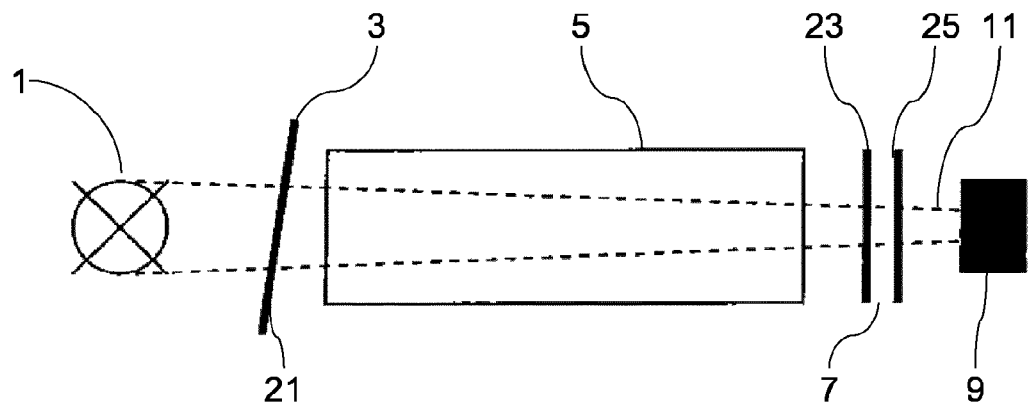
FIG. 1 is a schematic view showing a first exemplary embodiment of a device according to the present invention.

Referring to the drawings in particular, FIG. 1 shows a first exemplary embodiment of a device according to the present invention, which has a first radiation source 1, a first etalon 3, a first measuring section 5, a Fabry-Perot interferometer 7, and a detector 9, which are arranged along a first beam path 11. The first radiation source 1 is a thermal radiator (e.g., membrane radiator, helical radiator or Nernst stick), which has a continuous spectrum, whose maximum is at about 5 μm, over a spectral range of 2 μm to 20 μm.

Figure 7:
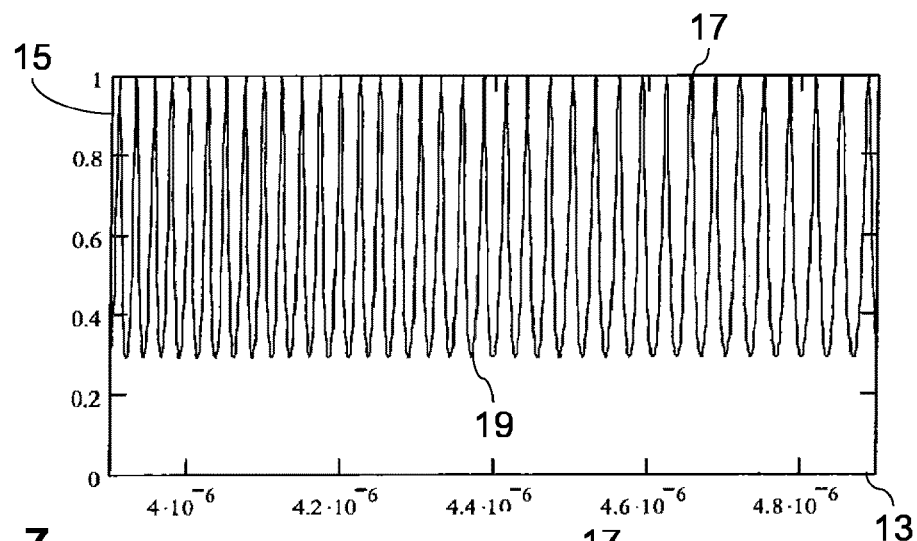
FIG. 7 is a graph showing a transmission spectrum of an etalon according to the first exemplary embodiment in a first spectral range.
Figure 8:
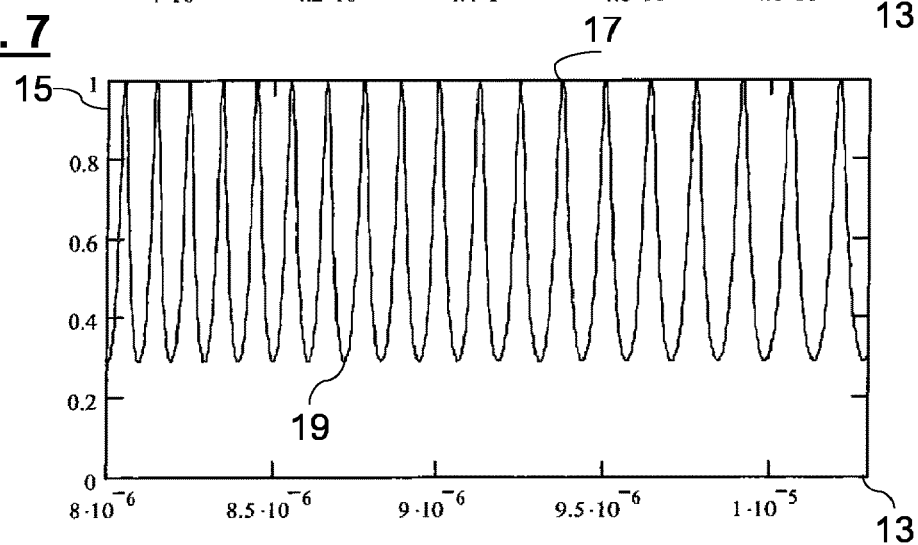
FIG. 8 is a graph showing a transmission spectrum of an etalon according to the first exemplary embodiment in a second spectral range.

The etalon 3 arranged behind the radiation source 1 in the direction of radiation propagation is comprised of a silicon wafer with a thickness of 100 μm, which transmits radiation in a first spectral range and in a second spectral range and has a plurality of transmission maxima in both spectral ranges. The calculated transmission of the etalon 3 in the first spectral range, which comprises the wavelengths of 4 μm to 5 μm, is shown in FIG. 7, the abscissa 13 showing the wavelength in m and the ordinate 15 showing the relative transmission. The etalon 3 has 35 transmission maxima 17 and just as many transmission minima 19 in the first spectral range. FIG. 8 shows the calculated transmission of the etalon 3 in the second spectral range, where the same reference numbers are used for identical elements in all drawings. The wavelength in m is shown in FIG. 8 on the abscissa 13 and the relative transmission of the etalon 3 is shown on the ordinate 15. The etalon 3 has 25 transmission maxima 17 and just as many transmission minima 19 in the second spectral range.

A first measuring section 5, which is, for example, a cuvette filled with a breathing gas, is arranged downstream in the direction of radiation propagation along the first beam path 11. The etalon 3 is arranged such that the surface 21 pointing toward the surface of the cuvette does not extend in parallel to this in order to avoid undesired etalon effects between the cuvette and the etalon 3.

The Fabry-Perot interferometer 7, which has first and second mirror surfaces 23, 25, wherein the first mirror surface 23 extends in parallel to the second mirror surface 25 and points towards same, is arranged downstream in the first beam path 11. The distance between the mirror surfaces 23, 25 of the Fabry-Perot interferometer 7 can be set such that the bandpass filter formed by the Fabry-Perot interferometer 7 transmits radiation in the first and second spectral ranges simultaneously.

Farther downstream in the direction of radiation propagation, a detector 9 is arranged, which measures the intensity of the radiation after this has passed through the etalon 3, the first measuring section 5 and the Fabry-Perot interferometer 7. The detector 9 may be, for example, a quantum detector or a thermal detector, for example, a pyroelectric sensor.

To record an absorption spectrum of the gas arranged in the first measuring section 5, the distance between the mirror surfaces 23, 25 is changed continuously such that the bandpass filter formed by the Fabry-Perot interferometer 7 scans the first and second spectral ranges simultaneously. At each point in time, the detector 9 records an intensity of the radiation, which can be attributed via the distance of the mirror surfaces 23, 25 of the Fabry-Perot interferometer 7 at this point in time to the wavelength that is transmitted by the bandpass filter formed by the Fabry-Perot interferometer 7 at that distance or it let through. The detector 9 consequently measures a superposition of the radiation transmitted in the first and second spectral ranges.

Figure 9:
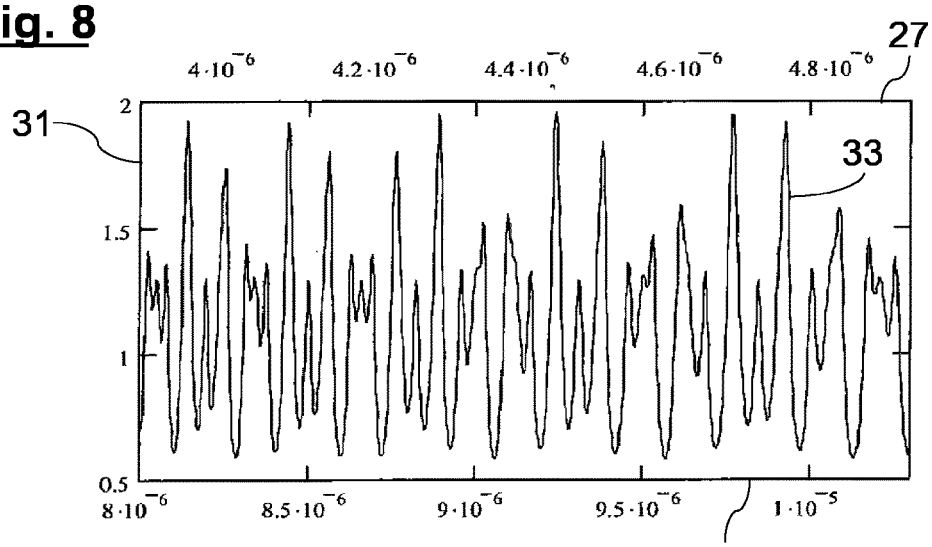
FIG. 9 is a graph showing a superposition of the transmission spectra shown in FIGS. 7 and 8.

FIG. 9 shows a corresponding superposition of the transmission spectra of the first etalon 3 in the first and second spectral ranges, where the upper abscissa 27 represents the wavelength in the first spectral range in m, the lower abscissa 29 shows the wavelength in the second spectral range, and the ordinate 31 shows the relative intensity of the radiation measured at the detector 9.

The first exemplary embodiment according to the present invention is especially advantageous, because it provides an especially compact device, which permits the absorption spectrum of a fluid to be recorded simultaneously with intensity-modified radiation in two spectral ranges without macromechanical components having to be used. Such devices require little maintenance, have a long service life and can be manufactured at a low cost.

To obtain the absorption spectra in the first and second spectral ranges, the measured signal 33, sent by the detector 9, must be separated. The difference of the frequencies of the transmission maxima 17 in the first and second spectral ranges, whose positions are, moreover, known, can be used for this. For example, the device may have a first lock-in amplifier and a second lock-in amplifier (not shown), with which the measured signal 33 can be compared with a reference signal suitable for each spectral range. For example, the measured signal 33 of a reference measurement in the respective spectral range may be used as a reference signal here.

It is also possible to separate the first and second spectral ranges by a Fourier analysis, where the difference in the frequency of the transmission maxima in the two spectral ranges is likewise used.

Figure 2:
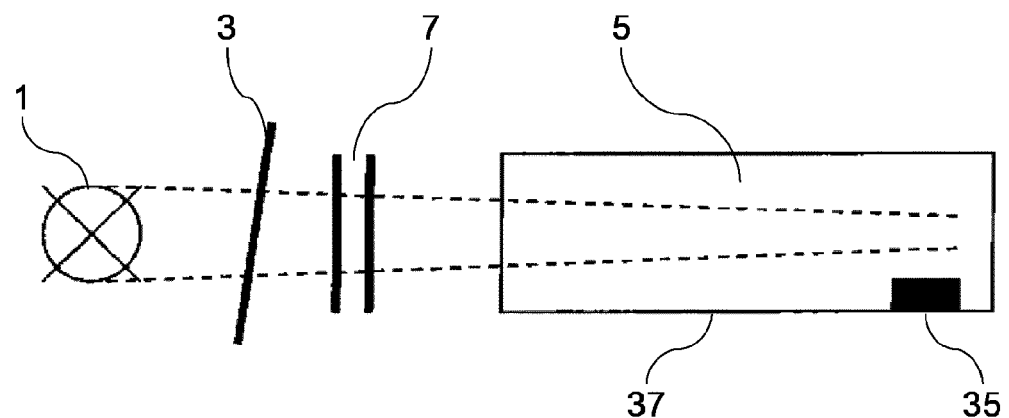
FIG. 2 is a schematic view showing a second exemplary embodiment of a device according to the present invention.

FIG. 2 shows a second exemplary embodiment of a device according to the present invention, in which the sequence of the Fabry-Perot interferometer 7 and the first measuring section 5 is transposed. In addition, the detector 35 is a broad-band photoacoustic sensor (e.g., microphone, cantilever, tuning fork-like crystal unit etc.), which is arranged in the cuvette 37 forming the first measuring section 5. The use of photoacoustic sensors is advantageous, because they permit the detection of the absorption spectra over a broad wavelength and dynamic range, on the one hand. On the other hand, a signal is generated only if an absorbing fluid is indeed present. Even small signals, i.e., only weak absorptions, can therefore still be detected with good contrast.

Figure 3:
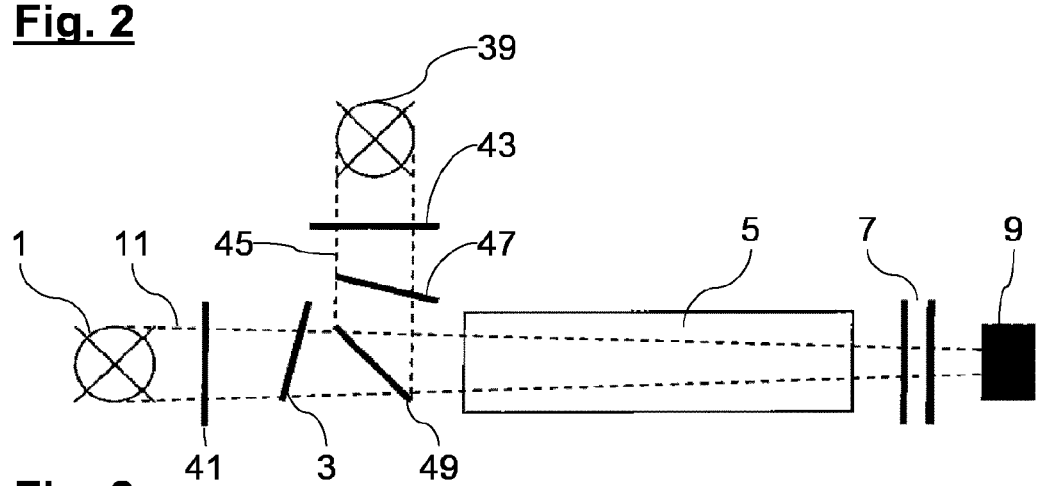
FIG. 3 is a schematic view showing a third exemplary embodiment of a device according to the present invention.

A third exemplary embodiment is shown in FIG. 3, in which a second radiation source 39 is provided next to the first radiation source 1. The first and second radiation sources 1, 39 are both broad-band thermal radiators, whose radiation is limited to the first and second spectral ranges by suitable bandpass filters 41, 43. The radiation emitted by the second radiation source 39 is passed through the device along a second beam path 45.

A first etalon 3 and a second etalon 47, which have a plurality of transmission maxima in the first and second spectral ranges, are arranged along the first and second beam paths 11, 45 behind the bandpass filter in the direction of propagation.

The radiations emitted by the first and second radiation sources reach the same beam splitter 49, which is arranged such that the first and second beam paths will extend downstream with one another or even in parallel through the first measuring section 5, which is made integrally with the second measuring section (coincides with same), and through the Fabry-Perot interferometer 7, and reach the same detector 9.

The exemplary embodiment shown in FIG. 3 is advantageous, because the first and second radiation sources 1, 39 can be connected independently from one another and it is thus possible in a simple manner to record absorption spectra in only one of the two spectral ranges.

It is also possible to use etalons 3 and 47 having different thicknesses, which permits the modulation in the first and second spectral ranges to be adapted, each separately, to the absorption spectrum of the fluid.

Figure 4:
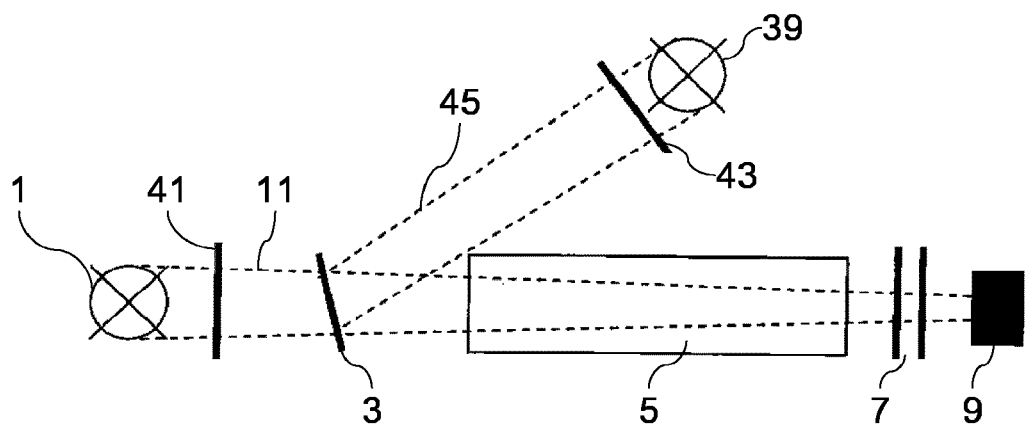
FIG. 4 is a schematic view showing a fourth exemplary embodiment of a device according to the present invention.

FIG. 4 shows a fourth exemplary embodiment, which is a variant of the third exemplary embodiment shown in FIG. 3. Only a first etalon 3 is used instead of a first etalon 3, a second etalon 47 and a beam splitter 49, and this etalon 3 is also used as a beam splitter and as an etalon in the first and second spectral ranges at the same time. The fact that an etalon also has the function of a bandpass filter when it reflects radiation is utilized in this case. The device according to the present invention shown in FIG. 4 is especially advantageous, because it has two independent radiation sources and it nevertheless has an especially compact design.

Figure 5:
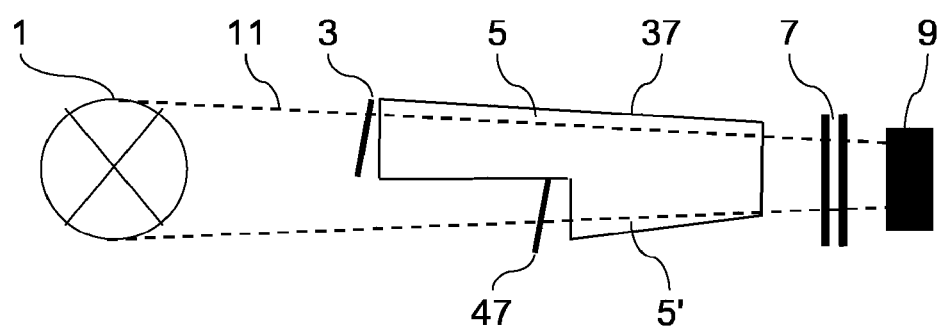
FIG. 5 is a schematic view showing a fifth exemplary embodiment of a device according to the present invention.

FIG. 5 shows a fifth exemplary embodiment, which shows the use of a first etalon and a second etalon 3, 47 in front of a cuvette 37, through which a gas flows, in which etalons 3, 47 the radiation passes through the gas along a first measuring section 5 and a second measuring section 5', wherein said first and second measuring sections 5, 5' have different lengths. This configuration has the advantage that gases with a small absorption cross section can be detected over the longer path but gases with a large absorption cross section can be detected over the shorter path simultaneously over a broad concentration range.

Figure 6:
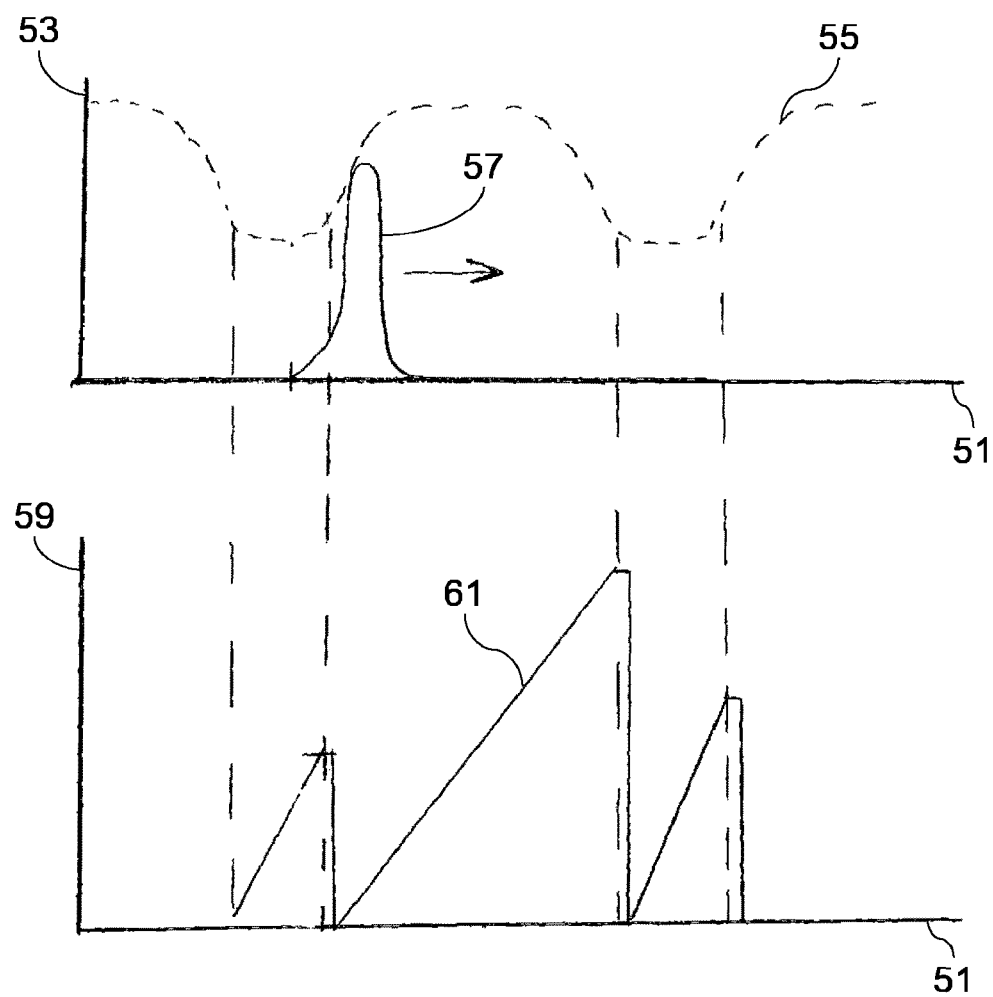
FIG. 6 are graphs showing aspects of a method for determining an absorption spectrum from a measured signal sent by a detector.

Finally, FIG. 6 schematically shows a method for determining an absorption spectrum from a measured signal. The wavelength is shown on the abscissa 51 and the transmission of the etalon and of the Fabry-Perot interferometer is shown on the ordinate 53 in the upper diagram in FIG. 6, the curve 55 drawn in broken line showing the transmission of the etalon and the solid curve 57 showing the transmission of the Fabry-Perot interferometer, which is being displaced from short towards long wavelengths. To determine the absorption spectrum, integration is performed over the intensity maxima and intensity minima during the recording of the measured signal. This is shown schematically in the lower diagram in FIG. 6, in which the wavelength is likewise shown on the abscissa 51 and the integrated measured signal 61 is shown on the ordinate 59. An absorption spectrum can be obtained from the value of the integral over a minimum and a maximum, whose positions are known, from the comparison with a reference measurement, and information can thus be obtained on the concentration of the components in a fluid. This method is especially advantageous, because the absorption spectrum of a fluid can be determined without the use of a lock-in amplifier being necessary.

While specific embodiments of the invention have been shown and described in detail to illustrate the application of the principles of the invention, it will be understood that the invention may be embodied otherwise without departing from such principles.

The invention claimed is:

1. A device for recording an absorption spectrum of a fluid, the device comprising:
    a radiation source, which emits radiation in a spectral range along a beam path;
    a first measuring section and a second measuring section, which are arranged in the beam path and along which the radiation passes through the fluid, the first measuring section comprising a first length, the second measuring section comprising a second length, the first length being different from the second length;
    a tunable Fabry-Perot interferometer, which is arranged in the beam path and which can transmit radiation in the spectral range as a displaceable bandpass filter;
    a detector for measuring the radiation in the spectral range;
    a first etalon, whose optical properties with respect to a transmitted wavelength range are not changed, for the spectral modulation of the radiation, which is arranged in the beam path and which has a plurality of transmission maxima in the spectral range, wherein the bandpass filter, formed by the Fabry-Perot interferometer, is displaceable over the spectral range such that the spectral modulation of the radiation by the first etalon is measured by the detector as a modulation of an intensity of the radiation over time so as to infer a transmitted wavelength and a wavelength of the radiation, the first etalon being arranged opposite the first measuring section;
    a second etalon arranged in the beam path, opposite the second measuring section, the first etalon and the second etalon being arranged on one side of the first measuring section and the second measuring section, the Fabry-Perot interferometer being arranged on another side of the first measuring section and the second measuring section, the one side being opposite the another side.

2. A device in accordance with claim 1, wherein a lock-in amplifier is provided for determining the absorption spectrum of the fluid from the radiation intensities measured with the detector, wherein said transmitted wavelength and said wavelength of the radiation are determined by an evaluation/data processing unit, the first etalon being located at a first distance from the Fabry-Perot interferometer, the second etalon being located at a second distance from the Fabry-Perot interferometer, the second distance being less than the first distance, the Fabry-Perot interferometer receiving radiation from the first measuring section and the second measuring section.

3. A device in accordance with claim 1, wherein the radiation source is a first radiation source and the radiation emitted thereby is along a first beam path and in a first spectral range, the first measuring section comprising a first measuring section first end area and a first measuring section second end area located opposite the first measuring section first end area, the first measuring section first end area and the first measuring section second end area defining at least a portion of the first beam path, the detection device is a first detection device, the device further comprising:
    a measuring structure comprising the first measuring section and the second measuring section
    a second radiation source, which emits radiation in a second spectral range along a second beam path, the second measuring section comprising a second measuring section first end area and a second measuring section second end area located opposite the second measuring section first end area, the second measuring section first end area and the second measuring section second end area defining at least a portion of the second beam path;
    a second detector for measuring the intensity of the radiation in the second spectral range, the radiation emitted by the second radiation source passing along the second measuring section through the fluid, arranged in the second beam path, wherein the first and second beam paths are designed such that the Fabry-Perot interferometer is arranged in the first and second beam paths and the Fabry-Perot interferometer transmits radiation in the second spectral range as a displaceable bandpass filter, the second etalon being provided for the spectral modulation of the radiation, which has a plurality of transmission maxima in the second spectral range, wherein the Fabry-Perot interferometer is set up such that the bandpass filter formed by the Fabry-Perot interferometer can be displaced over the second spectral range such that the spectral modulation of the radiation by the second etalon can be measured by the second detector as a modulation of the intensity of the radiation over time, each of said first etalon and said second etalon comprising an uncoated, polished thin wafer, said wafer comprising one of silicon and germanium, the first measuring section having a first measuring section length, the second measuring section having a second measuring section length, the first measuring section length being greater than the second measuring section length.

4. A device in accordance with claim 3, wherein:
    the Fabry-Perot interferometer is designed such that it can transmit radiation simultaneously in the first and second spectral ranges;
    the first measuring section, the second measuring section, the first etalon and the second etalon being arranged upstream of the Fabry-Perot interferometer with respect to the beam path; and
    the bandpass filter formed by the Fabry-Perot interferometer can be displaced simultaneously over the first and second spectral ranges such that the spectral modulation of the radiation by the first and second etalons can be measured by the first and second detectors as a modulation of the intensity of the radiation over time.

5. A device in accordance with claim 3, wherein:
    a first lock-in amplifier is provided for determining the absorption spectrum of the fluid from the radiation intensities measured with the first detector; and
    a second lock-in amplifier is provided for determining the absorption spectrum of the fluid from the radiation intensities measured with the second detector.

6. A device in accordance with claim 3, wherein the first etalon is made integrally with the second etalon.

7. A device in accordance with claim 3, wherein the first measuring section coincides with the second measuring section.

8. A device in accordance with claim 3, further comprising:
a measuring structure comprising the first measuring section and the second measuring section, the first etalon and the second etalon not extending parallel to an end surface of the measuring structure, wherein the first detector is made integrally with the second detector, the first measuring section comprising a first end surface, the second measuring section comprising a second end surface, the first etalon comprising a first etalon first planar surface and a first etalon second planar surface located opposite the first etalon first planar surface, the first etalon first planar surface and the first etalon second planar surface not being parallel to the first end surface, the second etalon comprising a second etalon first planar surface and a second etalon second planar surface located opposite the second etalon first planar surface, the second etalon first planar surface and the second etalon second planar surface not being parallel to the second end surface.

9. A device in accordance with claim 8, wherein the radiation source is made integrally with the second radiation source, the first etalon being arranged adjacent to a first area of the measuring structure, the second etalon being arranged adjacent to a second area of the measuring structure, the first area being located at an axially spaced location from the second area with respect to a longitudinal axis of the measuring structure.

10. A device in accordance with claim 9, wherein:
the first radiation source is a thermal radiator; and
the intensity of the first radiation source is modulated over time such that the relative change in the intensity of the radiation is more pronounced in one of the two spectral ranges than in the other spectral range.

11. A device in accordance with claim 1, wherein the radiation passes through the gas along the first measuring section and the second measuring section, the first etalon being located at a first distance from the radiation source, the second etalon being located at a second distance from the radiation source, the first distance being less than the second distance, the first measuring section being integrally connected to the second measuring section to define a one-piece measuring structure, the first measuring section comprising a first measuring section first end surface and a first measuring section second end surface, the first length being defined by the first measuring section first end surface and the first measuring section second end surface, the second measuring section comprising a second measuring section first end surface and a second measuring section second end surface, the second length being defined by the second measuring section first end surface and the second measuring section second end surface.

12. A method for recording an absorption spectrum of a fluid in a spectral range, the method comprising the steps of:
providing a device comprising:
a radiation source, which emits radiation in a spectral range along a beam path;
a first measuring section and a second measuring section, arranged in the beam path and along which the radiation passes through the fluid, the first measuring section comprising a first length, the second measuring section comprising a second length, the first length being different from the second length;
a tunable Fabry-Perot interferometer arranged in the beam path and which can transmit radiation in the spectral range as a displaceable bandpass filter;
a detector for measuring the radiation in the spectral range;
a first etalon, whose optical properties with respect to a transmitted wavelength range are not changed, for the spectral modulation of the radiation, arranged in the first beam path and which has a plurality of transmission maxima in the first spectral range, wherein the bandpass filter, formed by the Fabry-Perot interferometer, is displaceable over the spectral range such that the spectral modulation of the radiation by the first etalon is measured by the detector as a modulation of an intensity of the radiation over time, the first etalon being arranged opposite the first measuring section;
a second etalon arranged in the beam path, opposite the second measuring section, the first etalon and the second etalon being arranged on one side of the first measuring section and the second measuring section, the Fabry-Perot interferometer being arranged on another side of the first measuring section and the second measuring section, the one side being opposite the another side;
tuning the Fabry-Perot interferometer such that the bandpass filter formed by the Fabry-Perot interferometer is displaced over the spectral range;
measuring the spectral modulation of the radiation by the first etalon and the second etalon by the detector as a modulation of the intensity of the radiation over time;
deriving a transmitted wavelength and a wavelength of the radiation based on the intensity of the radiation over time.

13. A method in accordance with claim 12, wherein a measured signal is sent by the detector and is compared with a reference signal in a lock-in amplifier to determine the absorption spectrum in the spectral range, wherein said transmitted wavelength and said wavelength of the radiation are determined by an evaluation/data processing unit, the Fabry-Perot interferometer receiving radiation from the first measuring section and the second measuring section.

14. A method in accordance with claim 12, further comprising the steps of:
providing a measuring structure comprising the first measuring section and the second measuring section;
providing the radiation source as a first radiation source with the beam path being a first beam path and in a first spectral range and the detection device being a first detection device, the first measuring section comprising a first measuring section first end area and a first measuring section second end area located opposite the first measuring section first end area, the first measuring section first end area and the first measuring section second end area defining at least a portion of the first beam path;
providing a second radiation source, which emits radiation in a second spectral range along a second beam path, the second measuring section comprising a second measuring section first end area and a second measuring section second end area located opposite the second measuring section first end area, the second measuring section first end area and the second measuring section second end area defining at least a portion of the second beam path;
providing a second detector for measuring the intensity of the radiation in the second spectral range, the radiation emitted by the second radiation source passing along the second measuring section through the fluid, arranged in the second beam path wherein the first and second beam paths are designed such that the Fabry-Perot interferometer is arranged in the first and second beam paths and the Fabry-Perot interferometer transmits radiation in the second spectral range as a displaceable bandpass filter, the second etalon being provided for the spectral modulation of the radiation, which is arranged in the second beam path and which has a plurality of transmission maxima in the second spectral range, wherein the Fabry-Perot interferometer is set up such that the bandpass filter formed by the Fabry-Perot interferometer can be displaced over the second spectral range such that the spectral modulation of the radiation by the second etalon can be measured by the second detector as a modulation of the intensity of the radiation over time, each of said first etalon and said second etalon comprising an uncoated, polished thin wafer, said wafer comprising one of silicon and germanium, the first measuring section having a first measuring section length, the second measuring section having a second measuring section length, the first measuring section length being greater than the second measuring section length;

tuning the Fabry-Perot interferometer such that the bandpass filter formed by the Fabry-Perot interferometer is displaced over the second spectral range; and measuring the spectral modulation of the radiation by the second etalon by the second detector as a modulation of the intensity of the radiation over time.

15. A method in accordance with claim 14, wherein:
a first lock-in amplifier is provided for determining the absorption spectrum of the fluid from the radiation intensities measured with the first detector; and
a measured signal sent by the second detector is compared with a reference signal with a second lock-in amplifier to determine the absorption spectrum in the second spectral range.

16. A method in accordance with claim 14, wherein the Fabry-Perot interferometer is tuned such that the absorption spectrum of the fluid can be determined simultaneously in the first and second frequency ranges, the first measuring section, the second measuring section, the first etalon and the second etalon being arranged upstream of the Fabry-Perot interferometer with respect to the beam path.

17. A method in accordance with claim 14 wherein the first etalon is made integrally with the second etalon.

18. A method in accordance with claim 14, wherein the first measuring section coincides with the second measuring section.

19. A method in accordance with claim 14, further comprising:
a measuring structure comprising the first measuring section and the second measuring section, the first etalon and the second etalon not extending parallel to an end surface of the measuring structure, wherein the first detector is made integrally with the second detector, the first measuring section comprising a first end surface, the second measuring section comprising a second end surface, the first etalon comprising a first etalon first planar surface and a first etalon second planar surface located opposite the first etalon first planar surface, the first etalon first planar surface and the first etalon second planar surface not being parallel to the first end surface, the second etalon comprising a second etalon first planar surface and a second etalon second planar surface located opposite the second etalon first planar surface, the second etalon first planar surface and the second etalon second planar surface not being parallel to the second end surface.

20. A method in accordance with claim 19, wherein the first radiation source is made integrally with the second radiation source, the first etalon being arranged adjacent to a first area of the measuring structure, the second etalon being arranged adjacent to a second area of the measuring structure, the first area being located at an axially spaced location from the second area with respect to a longitudinal axis of the measuring structure.

* * * * *